United States Patent [19]

Green

[11] Patent Number: 4,665,916

[45] Date of Patent: May 19, 1987

[54] SURGICAL STAPLER APPARATUS

[75] Inventor: David T. Green, Norwalk, Conn.

[73] Assignee: United States Surgical Corporation, Norwalk, Conn.

[21] Appl. No.: 763,981

[22] Filed: Aug. 9, 1985

[51] Int. Cl.[4] ............................................ A61B 17/04
[52] U.S. Cl. .................................. 128/334 R; 227/19; 227/DIG. 1
[58] Field of Search ............... 128/334 R, 335, 334 C; 227/DIG. 1, 19

[56] References Cited

U.S. PATENT DOCUMENTS

| D. 271,714 | 12/1983 | Green ................... D24/27 |
| D. 271,796 | 12/1983 | Green ................... D24/27 |
| 3,079,606 | 3/1963 | Bobrov et al. ............ 1/120 |
| 3,080,564 | 3/1963 | Strekopitov et al. ....... 1/50 |
| 3,175,556 | 3/1965 | Wood et al. ............. 128/305 |
| 3,252,643 | 5/1966 | Strekopytov et al. ...... 227/109 |
| 3,269,630 | 8/1966 | Fleischer ............... 227/107 |
| 3,275,211 | 9/1966 | Hirsch et al. ........... 227/124 |
| 3,315,863 | 4/1967 | O'Dea ................... 227/19 |
| 3,317,105 | 5/1967 | Astafjev et al. ......... 227/76 |
| 3,490,675 | 1/1970 | Green et al. ............ 227/19 |
| 3,494,533 | 2/1970 | Green et al. ............ 227/19 |
| 3,499,591 | 3/1970 | Green ................... 227/76 |
| 3,589,589 | 6/1971 | Akopov .................. 227/153 |
| 3,665,924 | 5/1972 | Noiles et al. ........... 128/334 |
| 3,692,224 | 9/1972 | Astafiev et al. ......... 227/19 |
| 3,795,034 | 3/1974 | Strekopytov et al. ...... 29/212 D |
| 3,889,683 | 6/1975 | Kapitanov et al. ........ 128/305 |
| 3,935,981 | 2/1976 | Akopov et al. ........... 227/19 |
| 3,949,923 | 4/1976 | Akopov et al. ........... 227/19 |
| 4,047,654 | 9/1977 | Alvarado ................ 227/19 |
| 4,086,926 | 5/1978 | Green et al. ............ 128/334 R |
| 4,216,891 | 8/1980 | Behlke .................. 227/30 |
| 4,244,372 | 1/1981 | Kapitanov et al. ........ 128/334 R |
| 4,272,002 | 6/1981 | Moshofsky .............. 227/19 |
| 4,290,542 | 9/1981 | Fedotov et al. .......... 227/155 |
| 4,296,881 | 10/1981 | Lee ..................... 227/30 |
| 4,354,628 | 10/1982 | Green ................... 128/334 R |
| 4,378,901 | 4/1983 | Akopov et al. ........... 227/19 |
| 4,383,634 | 5/1983 | Green ................... 128/334 R |
| 4,397,311 | 8/1983 | Kanshin et al. .......... 128/305 |
| 4,402,444 | 9/1983 | Green ................... 227/19 |
| 4,415,112 | 11/1983 | Green ................... 128/334 R |
| 4,429,695 | 2/1984 | Green ................... 128/305 |
| 4,485,811 | 12/1984 | Chernousov et al. ....... 128/303.1 |
| 4,506,670 | 3/1985 | Crossley ................ 128/334 R |
| 4,506,671 | 3/1985 | Green ................... 128/334 R |
| 4,508,253 | 4/1985 | Green ................... 128/334 R |

FOREIGN PATENT DOCUMENTS

| 736256 | 6/1966 | Canada ................ 128/335 |
| 869527 | 3/1953 | Fed. Rep. of Germany . |
| 906791 | 9/1962 | United Kingdom . |
| 209629 | 3/1968 | U.S.S.R. . |
| 371926 | 5/1973 | U.S.S.R. . |
| 549145 | 5/1977 | U.S.S.R. . |

OTHER PUBLICATIONS

*Stapling Techniques in Gynecologic Surgery*, United States Surgical Corporation, 1975, pp. 8–10.

Primary Examiner—Richard C. Pinkham
Assistant Examiner—Gary Jackson
Attorney, Agent, or Firm—Thomas R. Bremer

[57] ABSTRACT

Surgical stapler apparatus for forming an array of surgical fasteners in body tissue includes an anvil assembly against which the fasteners are formed and a fastener holder pivotally mounted adjacent one end of the anvil assembly, a spacer member at the other end so constructed to displace tissue that would otherwise obstruct the spacer member from properly positioning the fastener holder relative to the anvil assembly to ensure proper fastener formation, and a knife assembly to cut the tissue between the rows of formed fasteners.

16 Claims, 13 Drawing Figures

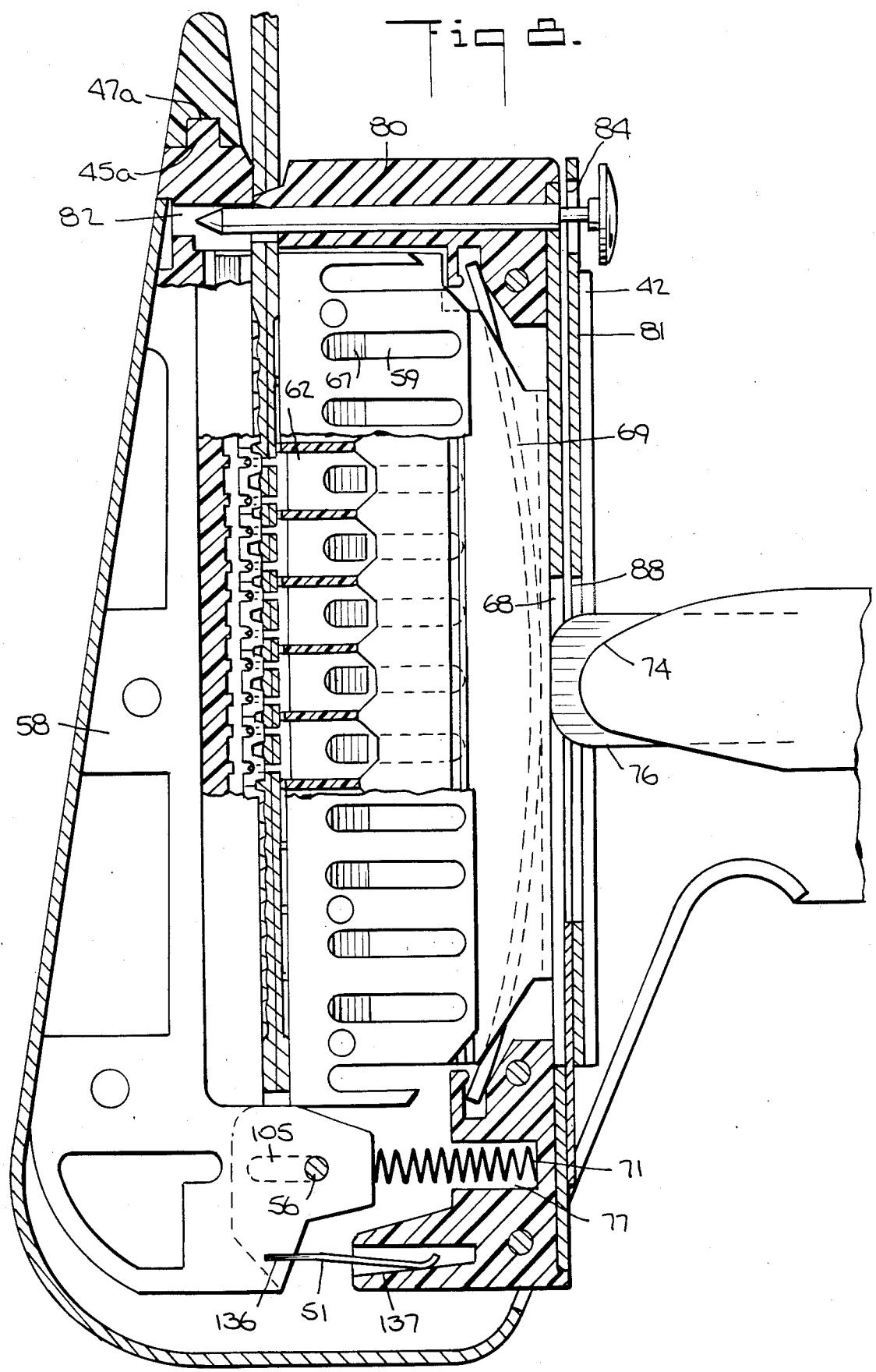

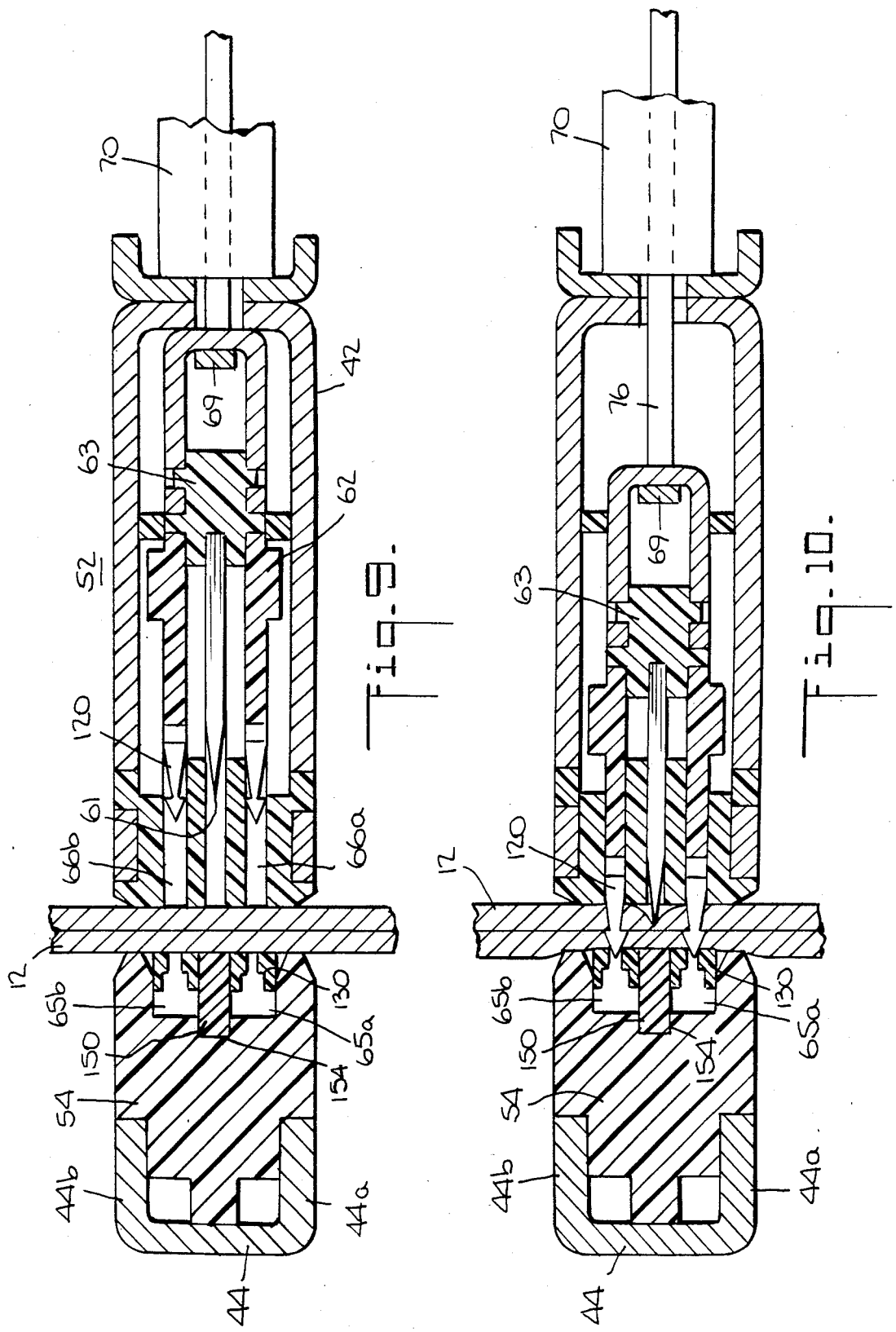

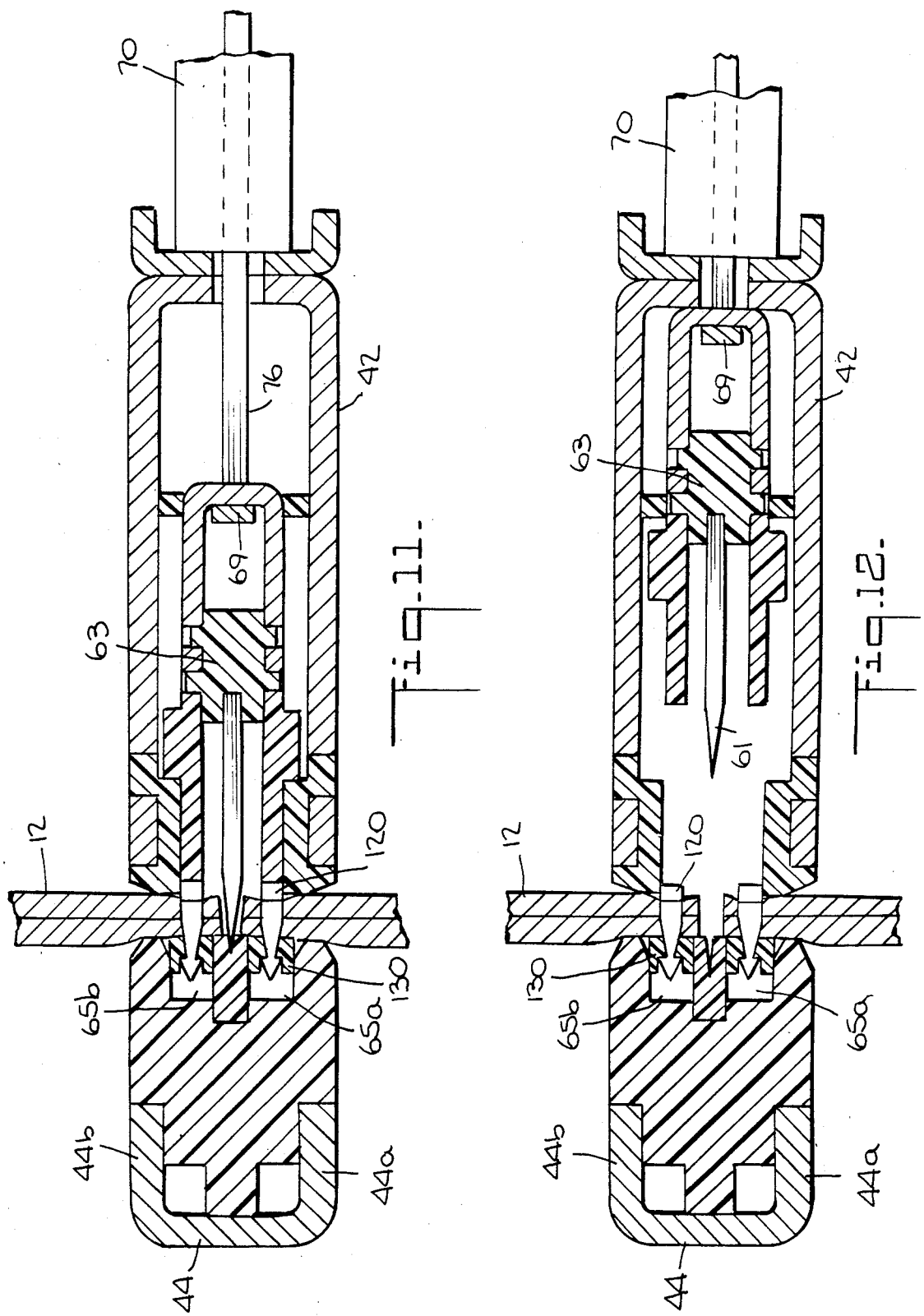

SURGICAL STAPLER APPARATUS

BACKGROUND OF THE INVENTION

This invention relates to surgical stapling apparatus, and more particularly to surgical stapling apparatus for substantially simultaneously applying a plurality of surgical fasteners to body tissue.

Surgical stapling apparatus in which a plurality of surgical fasteners are applied substantially simultaneously to produce an array of surgical fasteners are known. Typically these apparatus include a fastener holder disposed on one side of the tissue to be fastened, an anvil assembly parallel to the fastener holder on the other side of the tissue to be fastened, means for linearly translating the fastener holder and the anvil assembly toward one another so that the tissue is clamped between them, and means for driving the fasteners from the fastener holder so that the ends of the fasteners pass through the tissue and form finished fasteners as they make contact with the anvil assembly, thereby producing an array of finished fasteners in the tissue. The term "fasteners" is used herein as a generic term for metal surgical staples, the staple-shaped portion of two-part resinous surgical fasteners, and their equivalents. Similarly, the term "anvil assembly" is used herein as a generic term to include the anvil used to clinch metal surgical staples, the retainer holder and retainer member of two-part resinous surgical fasteners, and the equivalent of these elements.

In common use are apparatus in which the fastener holder and anvil assembly comprise a disposable cartridge removably mounted in or on a permanent actuator for supporting and actuating the cartridge. The cartridge is disposable after a single use. The permanent actuator is reusable in the same surgical procedure after reloading with a fresh cartridge, and is reusable in another surgical procedure after cleaning, sterilizing, and reloading. Also available are disposable surgical apparatus, in which the cartridge and actuator are preassembled, ready for use, and are then disposed of after a single use.

In the use of these apparatus it is of great importance that the fastener hoder and anvil assembly be positioned accurately and precisely in relation to each other, so that the tissue joining procedure occurs in a proper manner. In surgical stapler apparatus of the type disclosed in commonly-assigned Green U.S. Pat. No. 4,354,628, it is intended that the tissue to be stapled be enclosed completely between the stapler holder and the anvil assembly (as shown in FIG. 4 of that patent), i.e., none of the tissue extends past the end of the staple holder and anvil assembly. This permits the staple holder and anvil assembly to be positioned accurately relative to each other by means of a spacer member disclosed and claimed in that patent. There are, however, certain surgical procedures in which it is not possible to enclose the tissue to be stapled completely within the two legs of the stapler. In such circumstances the tissue extending beyond the legs of the stapler would prevent the spacer member from abutting against the anvil assembly and could result in improperly formed fasteners.

It is known, using instruments of the type shown in commonly-assigned Green U.S. Pat. No. 3,494,533, to apply the surgical fasteners to tissue where the tissue extends beyond the ends of the legs of the stapler. In such circumstances, an alignment pin either is forced through the tissue, if the tissue is sufficiently soft, or the surgeon must manually cut the tissue prior to pushing the alignment pin through the tissue. The cartridge and anvil used with instruments of the type disclosed in U.S. Pat. No. 3,494,533 are aligned parallel to each other through the parallel positioning of the legs of the instrument on which the cartridge and anvil are located.

As noted in U.S. Pat. No. 4,354,628, proper alignment between the fastener holder and anvil assembly of that patent is maintained primarily by these elements themselves, and it is desired not to rely on the instrument to provide that alignment. It is therefore an object of the instant invention to provide surgical stapling apparatus of the type shown in U.S. Pat. No. 4,354,628 in which there is provided means which ensures that the fastener holder and anvil assembly are substantially parallel to each other even when the tissue to be joined extends beyond the stapling apparatus.

SUMMARY OF THE INVENTION

This and other objects of the invention are accomplished in accordance with the principles of the invention by providing surgical stapling apparatus in which a spacer member on the fastener holder displaces the tissue which would otherwise prevent it from abutting properly against the anvil assembly. alignment pin is shaped also so as to ensure that it can be pushed through the tissue and into the distal portion of the stapler. Proper relative positioning of the fastener holder and anvil assembly is thereby maintained without requiring additional manual steps by the surgeon, thus enabling the patient to spend less time in the operating room. The stapler apparatus also decreases the trauma to the tissue by displacing the tissue in a manner improved from the previously known technique by avoiding the need, with some surgical procedures, to cut the tissue before pushing the alignment pin through.

Further features of the invention, its nature and various advantages will be more apparent from the accompanying drawing and the following detailed description of the invention.

BRIEF DESCRIPTION OF THE DRAWING

FIG. 4A is an enlarged perspective view of a part of the cartridge of FIG. 4 showing the spacer member of the invention.

FIG. 8 is a view similar to FIGS. 5–7 showing how the knife-fastener pusher member retracts into the fastener holder after the tissue has been joined.

FIG. 9 is a top sectional view showing the conditon of the apparatus with the tissue clamped and ready to be fastened, similarly to FIG. 6.

FIG. 10 is a top sectional view similar to FIG. 9 showing the fastener prongs entering the retainers and the knife beginning to cut the tissue.

FIG. 11 is a top sectional view similar to FIGS. 9 and 10 showing the fastener prongs inserted fully into the retainers and the knife having cut completely through the tissue.

FIG. 12 is a top sectional view similar to FIGS. 9–11 showing the knife-fastener pusher member in its retracted position, as also shown in FIG. 8.

DETAILED DESCRIPTION OF THE INVENTION

Although the principles of the invention are applicable to other similar types of surgical stapler apparatus, the invention will be understood clearly from an explanation of its application to the surgical stapler apparatus of the type mentioned above. The invention is applicable also to both permanent and disposable apparatus. Accordingly, although the invention will be illustrated in an embodiment in which a disposable cartridge comprising a fastener holder and an anvil assembly is mounted in a permanent instrument, the invention could equally be described in use in a totally disposable embodiment.

The surgical stapler apparatus of this invention may be of the type shown in commonly assigned Green U.S. Pat. No. 4,354,628. The preferred embodiment is of such a surgical stapler apparatus and the entire disclosure of that patent is incorporated herein by reference. That patent discloses and claims a tissue block spacer member as to which the present invention is an improvement, permitting the stapler to be used in surgical techniques in which the entire tissue is not encompassed in the area between the fastener holder and anvil assembly.

Figure 1:
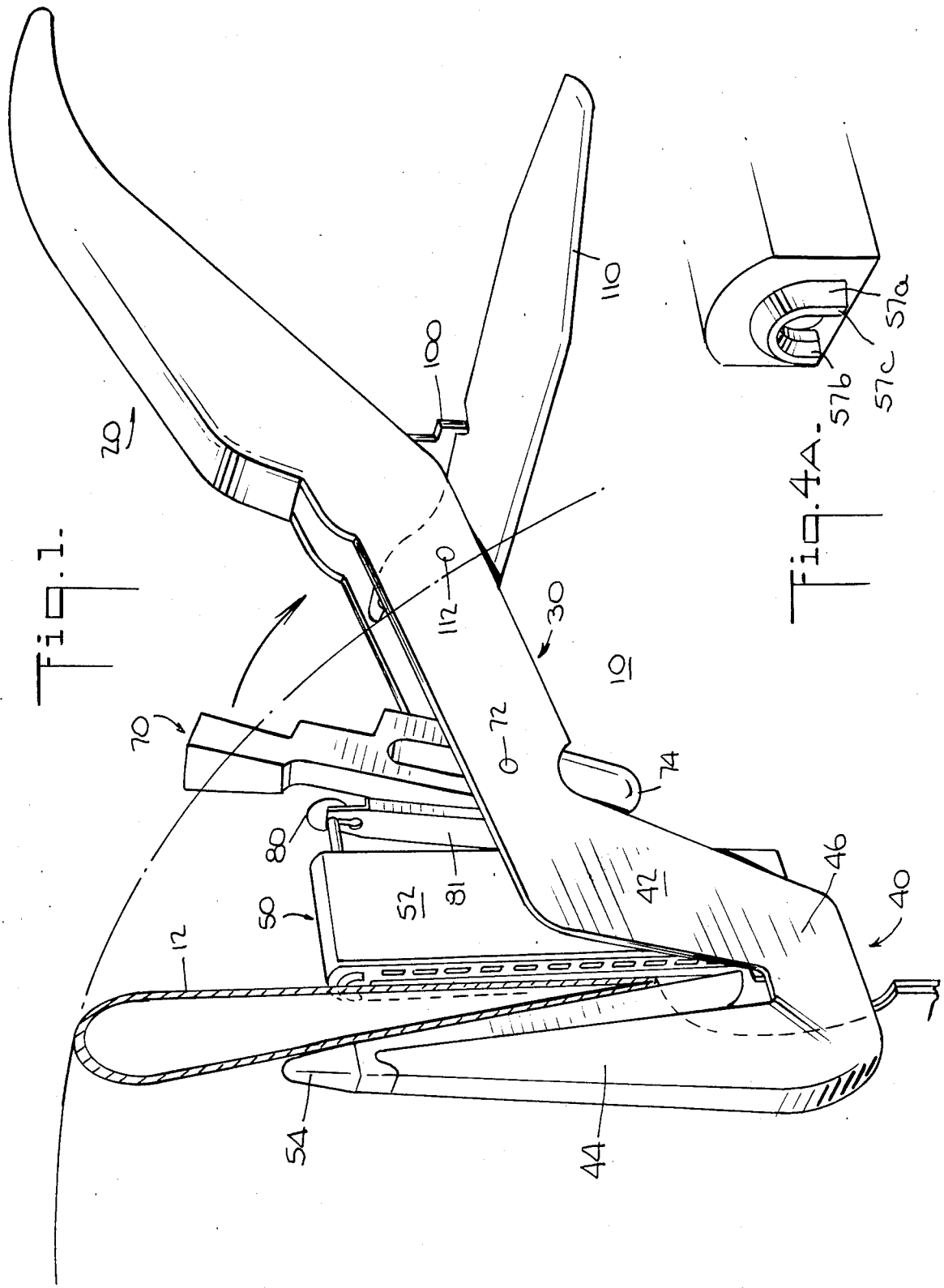
FIG. 1 is a perspective view of a surgical stapler apparatus constructed in accordance with the invention.

As shown in FIG. 1, instrument 10 includes handle 20 adjacent the proximal end of the instrument, a longitudinal connecting structure 30 at approximately a 30°–45° angle to handle 20, and an open U-shaped or V-shaped support structure 40 at the distal end of connecting structure 30. As is better seen in FIG. 3, support structure 40 comprises a proximal leg 42, a distal leg 44, and a base 46 joining one end of each of legs 42 and 44. Support structure 40 lies in a plane substantially parallel to the longitudinal axis of connecting structure 30. In use, the instrument is positioned relative to tissue 12 to be fastened, e.g., in gynecologic surgery, so that the tissue is generally between legs 42 and 44 and transverse to the plane of support structure 40. In contrast to prior known uses for surgical staplers of this type having spacer members, it is intended that tissue 12 will extend past the open ends of legs 42 and 44. The use of known staplers of the type shown in U.S. Pat. No. 4,354,628 has been limited to procedures in which the entire tissue could be contained between legs 42 and 44. There are, however, certain operations where it either is not desirable or possible to place the stapler around the entire tissue, and this invention enables this stapler to be used for such procedures.

Figure 2:
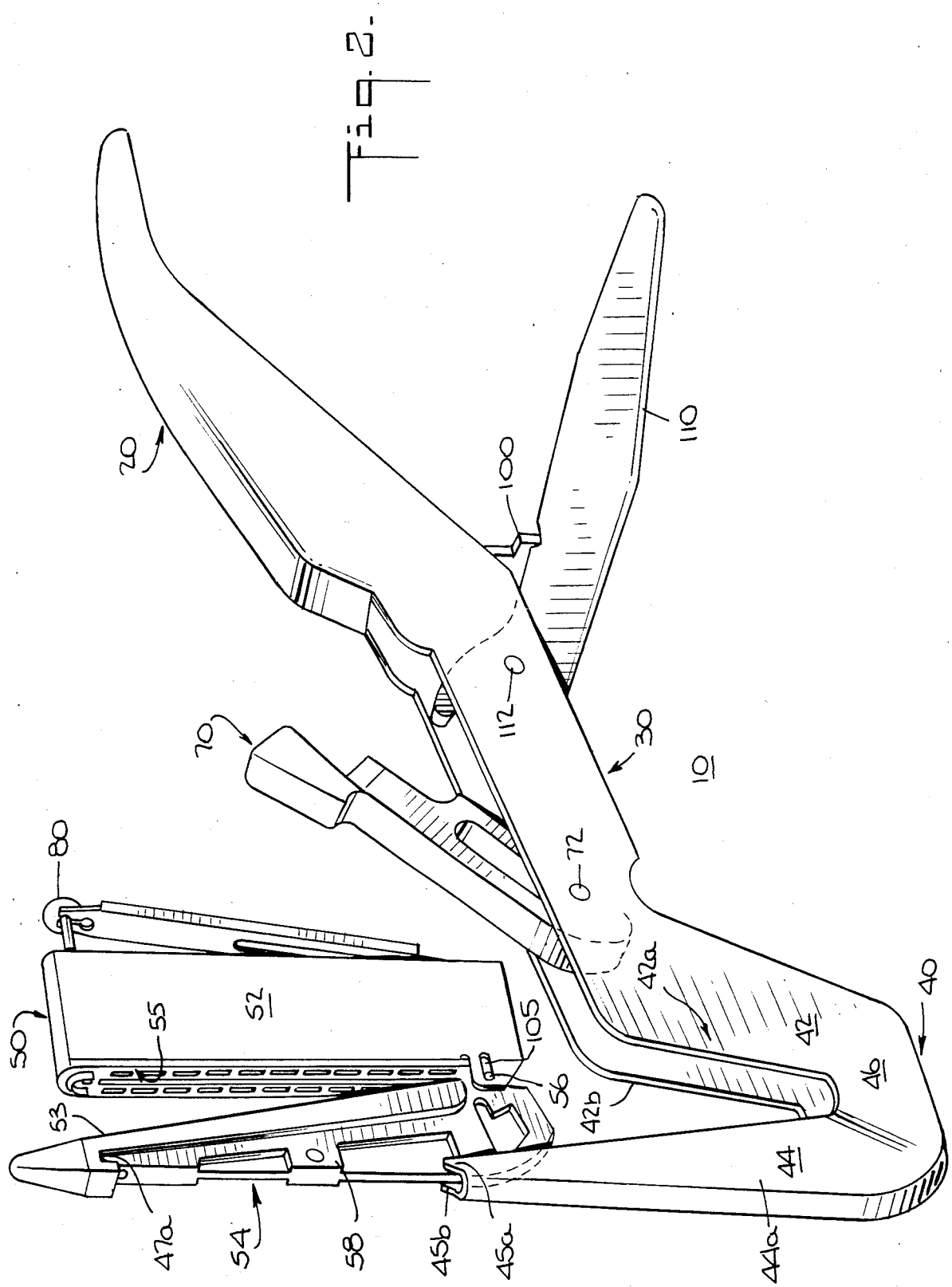
FIG. 2 is a perspective view of the surgical stapler apparatus of FIG. 1 showing how the cartridge is placed into the stapler.

As is more clearly seen in FIG. 2, the disposable cartridge 50 includes fastener holder 52 and anvil assembly 54. Anvil assembly 54 is mounted into distal leg 44 and fastener holder 52 is mounted into proximal leg 42. The end of cartridge 50 at which pivotal axis 56 is located is inserted into base 46. Pivotal axis 56 allows pivotal motion of fastener holder 52 and anvil assembly 54 relative to each other and, together with slots 105, also allows a limited amount of motion of the fastener holder perpendicular to anvil assembly surface 53.

Anvil assembly 54 is designed to slide longitudinally into and out of leg 44 of support structure 40. The distal side of anvil assembly 54 has a distally projecting retaining structure 58 which fits between plates 44a and 44b of distal leg 44. Cartridge 50 is releasably retained to leg 44 by a friction fit between retaining structure 58 and plates 44a and 44b, and is positioned accurately in the longitudinal direction on leg 44 by the fit between projections 45a and 45b and cut outs 47a and 47b (not shown) at the corresponding ends of anvil assembly 54. When cartridge 50 is positioned in support structure 40 and projections 45a and 45b are located against cut outs 47a and 47b, anvil assembly 54 will be located between plates 42a and 42b of proximal leg 42.

Figure 4:
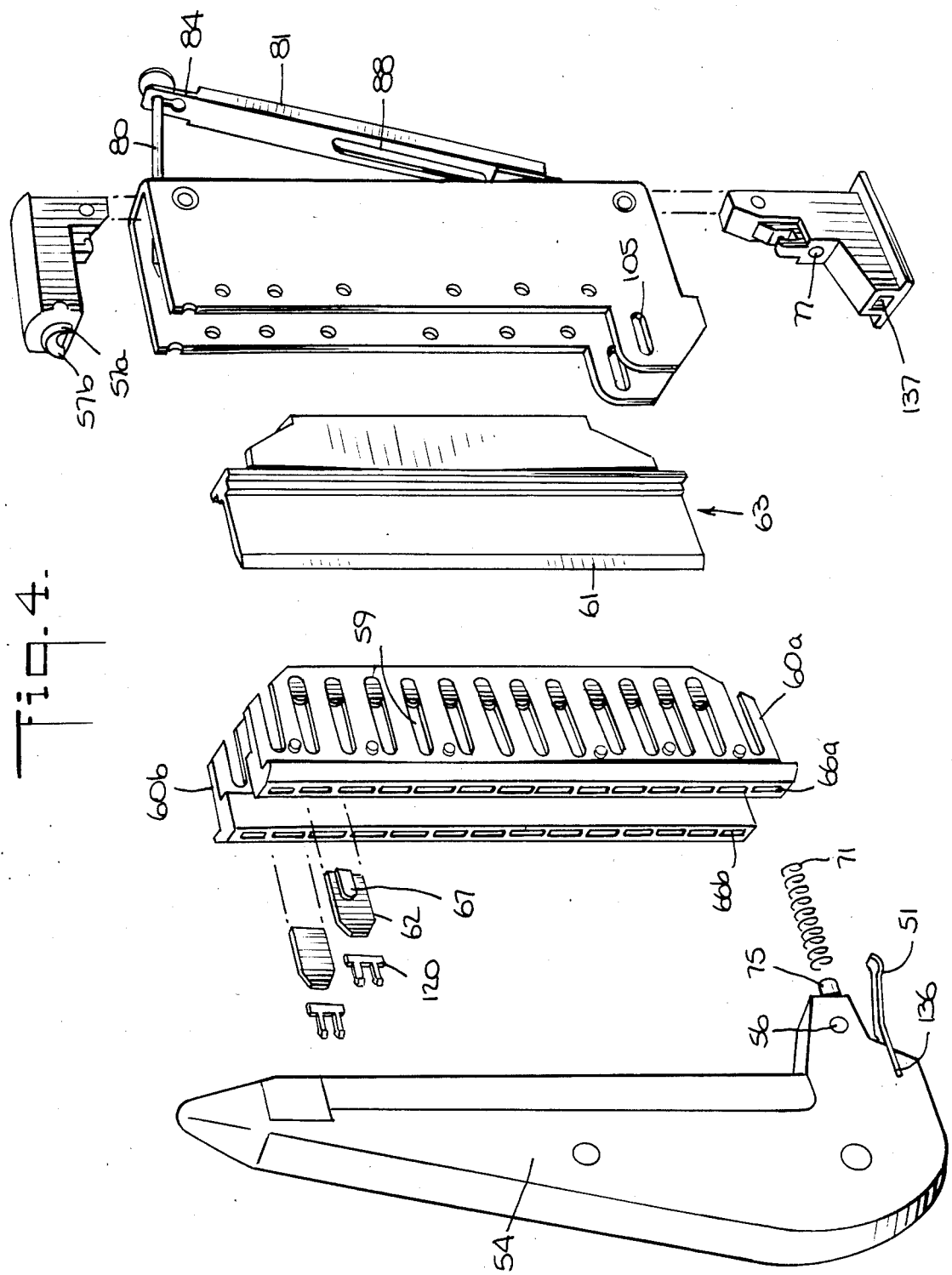
FIG. 4 is an exploded perspective view of the cartridge constructed in accordance with the invention.

As shown, for example, in FIG. 9, anvil assembly 54 has two parallel rows of retainer-containing apertures 65a and 65b which are respectively aligned with two rows of fastener-containing apertures 66a and 66b located in fastener holder 52. Each fastener containing aperture initially contains one fastener 120, and each retainer-containing aperture initially contains one retainer 130. The apertures are further aligned so that one retainer in the associated row of retainers is opposite one fastener in the associated row of fasteners. The two prongs of the fastener are aligned with the two apertures in the retainer. Behind each fastener is a fastener pusher 62 slidably mounted in pusher holders 60a and 60b (see FIG. 4). During ejection of the fasteners, the proximal ends of fastener pushers 62 all contact knife-fastener pusher member 63 which also is slidably mounted in fastener holder 52. Fastener pushers 62 are guided along in the distal direction by slots 59 in pusher holders 60a and 60b into which projections 67 of fastener pushers 62 extend. Access to knife-fastener pusher member 63 is through elongated slot 68 in the proximal side of fastener holder 52 and elongated slot 88 in spring 81, to be discussed in more detail below. Fastener holder 52 normally is biased away from anvil assembly 54 as shown, for example, in FIG. 5, by leaf spring 51 and spring 71. As seen in FIG. 4, one end of leaf spring 51 is mounted in tongue 136 in anvil assembly 54. The other end of leaf spring 51 bears against surface 137 inside fastener holder 52. Spring 71 biases pivotal axis 56 to the distal end of slots 105, and is kept in place by projection 75 and cylindrical space 77.

Fastener holder 52 also carries alignment pin 80. In order to prevent the end of alignment pin 80 from partly obstructing the open end of cartridge 50 when that cartridge is open, and thereby presenting a possible hazard to the tissue being placed in or removed from the instrument, alignment pin 80 is reciprocally mounted in fastener holder 52 and provided with means for automatically extending the pin during the stapling operation and automatically retracting the pin when cartridge 50 is opened. As shown, for example, in FIG. 4, the proximal end of pin 80 is engaged by the slotted end 84 of leaf spring 81 which extends along the proximal side of fastener holder 52 and is anchored at the bottom of fastener holder 52. Leaf spring 81 has an elongated slot 88 which is generally co-extensive with slot 68 in fastener holder 52. Leaf spring 81 is arranged so that it is normally inclined away from the proximal side of fastener holder 52 in the direction toward pin 80 as shown, for example, in FIGS. 2 and 4. In this condition, spring 81 holds pin 80 in the retracted position so that distal end 86 of pin 80 does not project from fastener holder 52. Distal end 86 of alignment pin 80 is conically-shaped. This enables alignment pin 80 to pierce tissue 12 as the pin is extended beyond fastener holder surface 55 during the stapling operation.

When tissue 12 is in place between fastener holder 52 and anvil assembly 54, pivoting clamp actuator 70 is pivoted clockwise about its pivotal axis 72 as shown in FIG. 1. This causes camming surface 74 on the distal end of actuator 70 to pivot fastener holder 52 counter-clockwise about its pivotal axis 56, thereby gradually clamping tissue 12 between fastener holder 52 and opposing anvil assembly surface 53.

Figure 3:
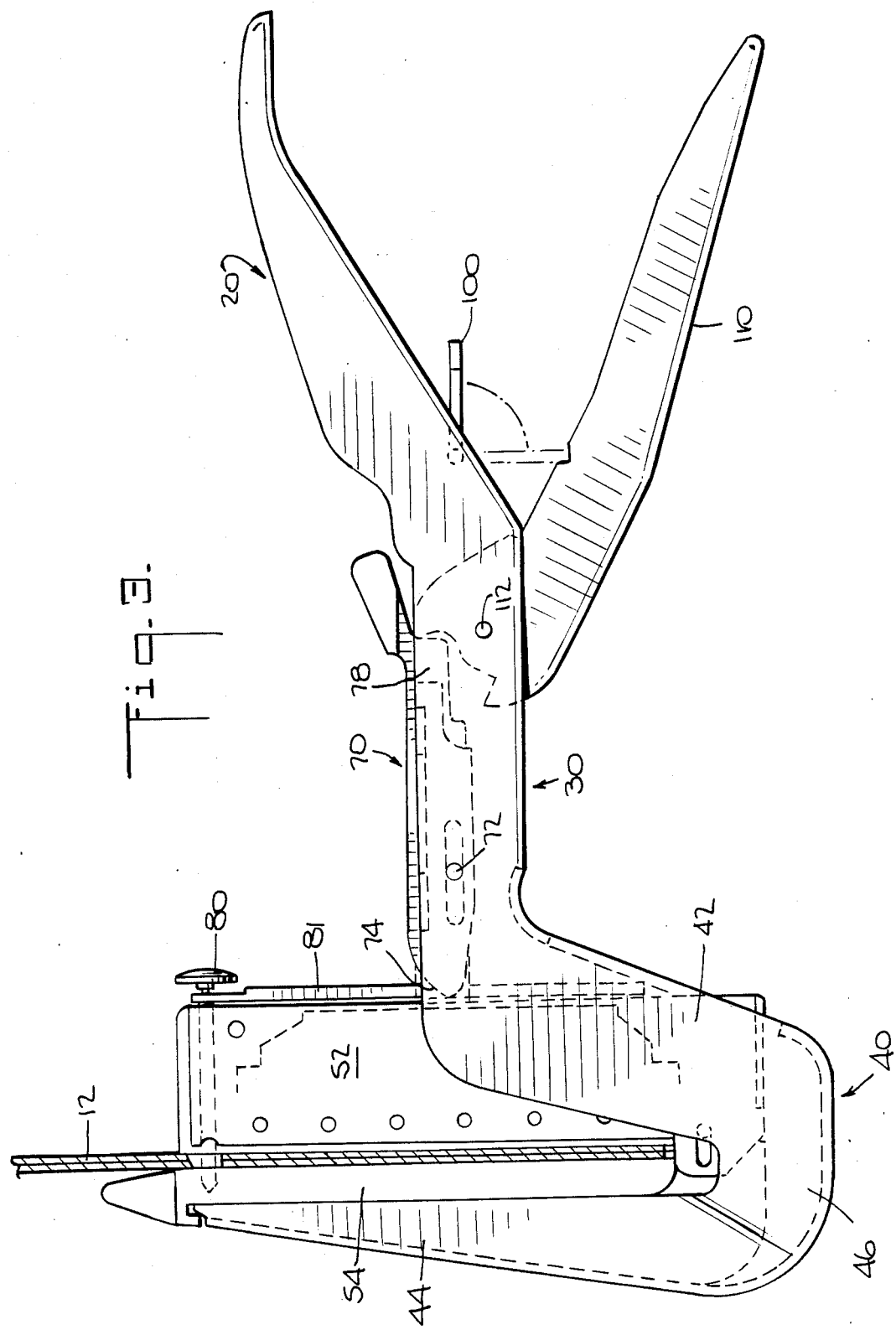
FIG. 3 is an elevational view of the apparatus of FIG. 1 showing the apparatus in use with tissue clamped and ready for fastening.
Figure 5:
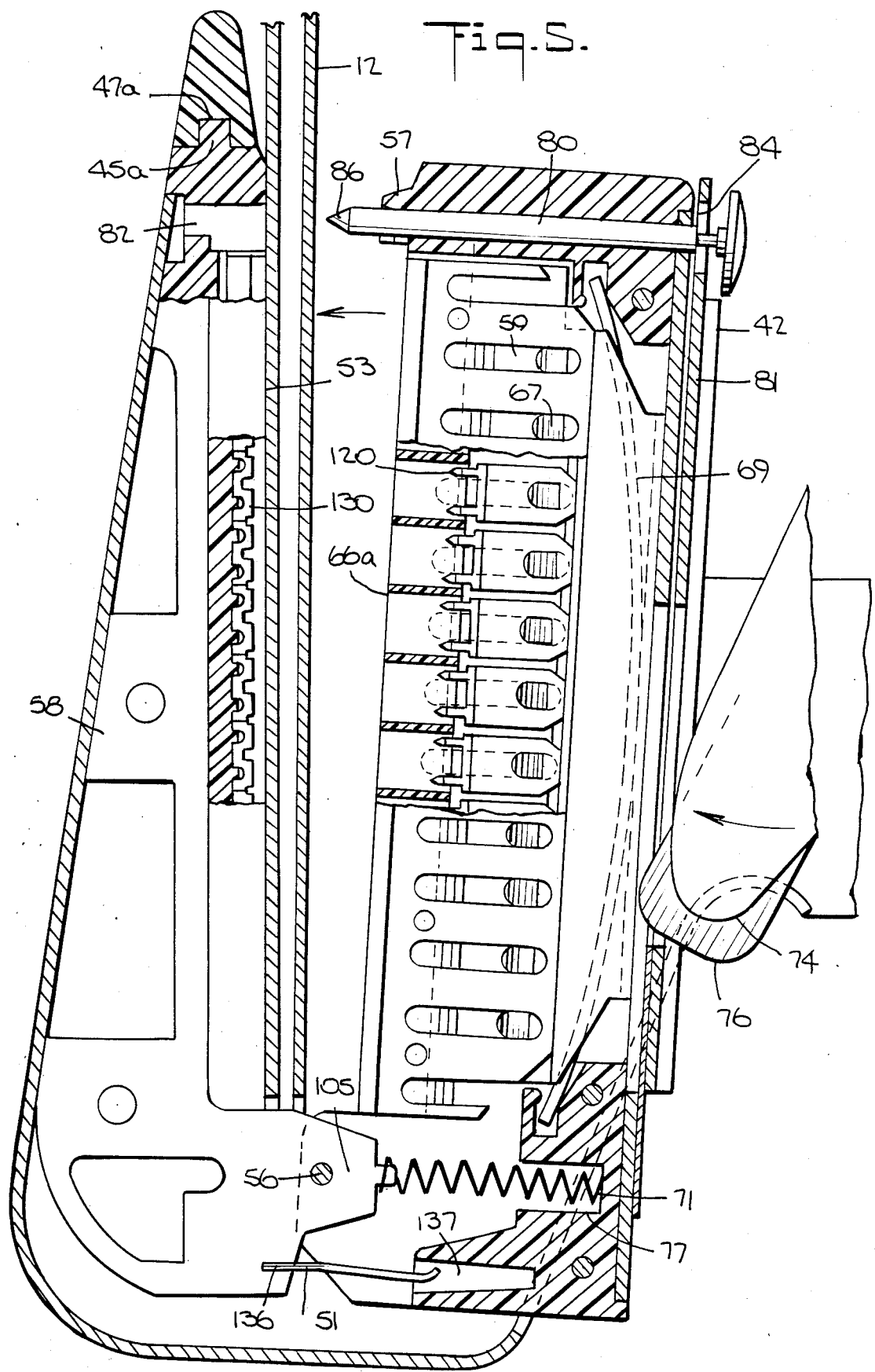
FIG. 5 is an enlarged elevational sectional view of a part of the apparatus of FIG. 1 showing how the apparatus is operated to clamp the tissue to be fastened.

When actuator 70 has been fully pivoted clockwise so that it is substantially parallel to the longitudinal axis of connecting structure 30 as shown in FIG. 3, tissue 12 is then firmly clamped between anvil assembly surface 53 and opposing fastener holder surface 55. As fastener holder 52 closes on tissue 12 being clamped as shown in FIG. 5, alignment pin 80 pierces the tissue and spacer member 57 displaces the tissue surrounding pin 80 and contacts anvil assembly surface 53. Elongated apertures 105 allow pivotal axis 56 to translate linearly in the proximal direction by a small amount as indicated by arrow 64 in FIG. 5, thereby resulting in fastener holder surface 55 and anvil assembly surface 53 being parallel and ready for firing of fasteners 120.

Figure 6:
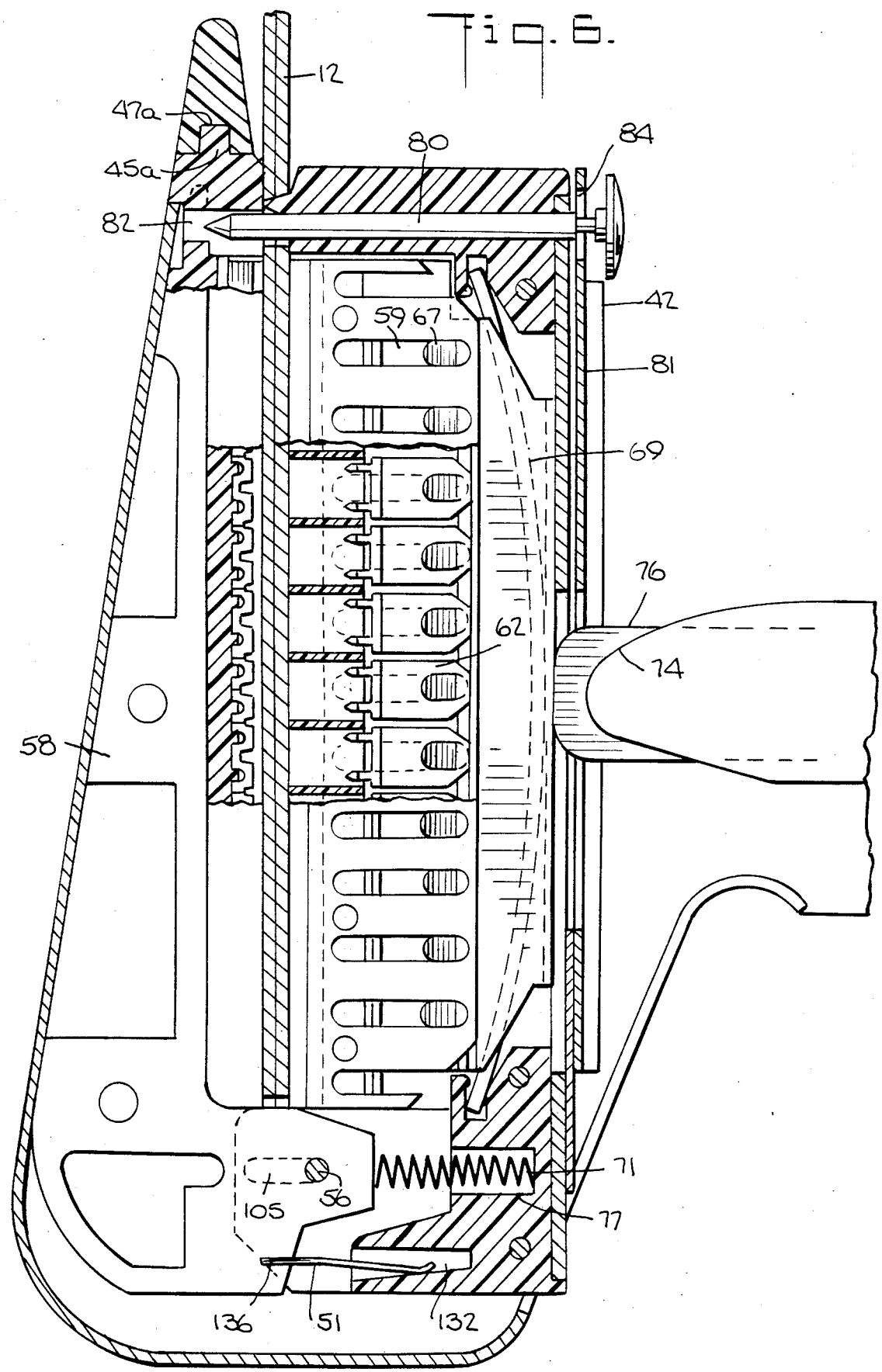
FIG. 6 is a view similar to FIG. 5 showing the condition of the apparatus with the tissue clamped and ready to be fastened.
Figure 7:
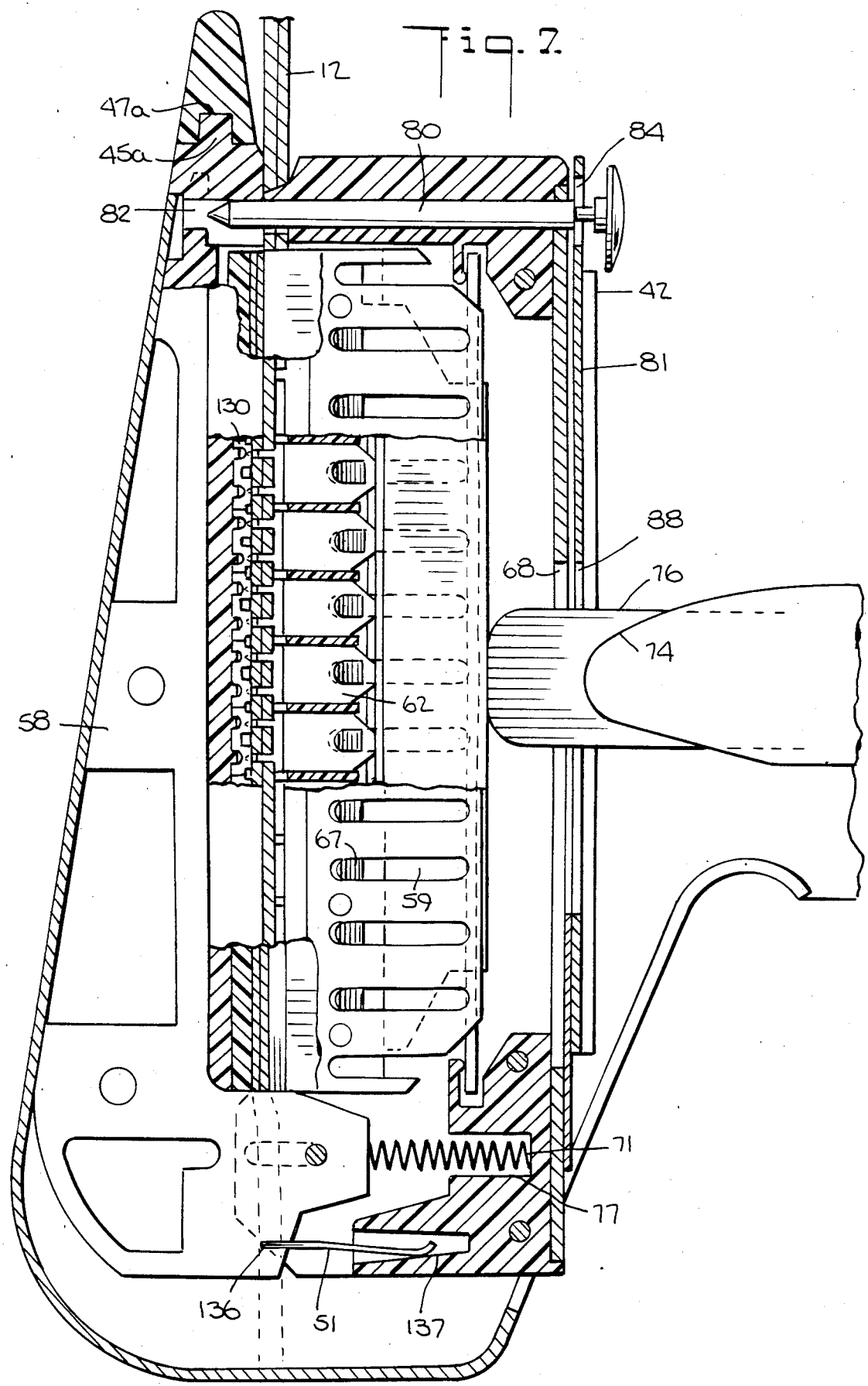
FIG. 7 is a view similar to FIGS. 5 and 6 showing how the apparatus operates to fasten the clamped tissue.

In previous devices available, the presence of tissue extending beyond the stapler would prevent spacer member 57 from contacting anvil assembly surface 53 and thereby possibly interfere with proper firing of the fasteners. In the invention, however, as fastener holder 52 is rotated counter-clockwise by actuator 70 the tissue that would otherwise prevent spacer member 57 from contacting anvil assembly surface 53 is displaced by sloping surfaces 57a and 57b of spacer member 57 (see FIG. 4A). These surfaces slope towards each other to form a knife-like edge to displace the tissue and act to permit furthest-most projection i.e. surface- 57c of spacer member 57 to abut against anvil assembly surface 53. Proper alignment of fastener holder 52 and anvil assembly 54 is aided by alignment pin 80 which extends through the side of fastener holder 52 opposite pivotal axis 56 and into alignment pin aperture 82 in anvil assembly 54 as fastener holder surface 55 is pivoted parallel to anvil assembly surface 53. As fastener holder 52 is pivoted counter-clockwise alignment pin 80 extends past spacer member 57 and makes contact with and pushes through the tissue located in front of the alignment pin aperture 82 in the anvil assembly (see FIG. 5). As fastener holder 52 continues to pivot counter-clockwise spacer member 57 reaches the tissue and begins to displace the tissue which is now surrounding alignment pin 80. When fastener holder 52 is fully pivoted, as shown in FIG. 6, spacer member 57 has displaced the tissue so as to abut against anvil assembly surface 53 and ensure parallel alignment between fastener holder surface 55 and anvil assembly surface 53.

Also, when actuator 70 is fully pivoted clockwise as shown in FIG. 3, driver 76, which is carried by actuator 70, also is substantially parallel to the longitudinal axis of connecting structure 30. The distal end of driver 76 then extends into the proximal side of fastener holder 52 and is adjacent the proximal surface of knife-fastener pusher member 63 in the fastener holder. Safety latch 100, which normally keeps actuator lever 110 pivoted clockwise away from handle 30, is now released by pivoting it counter-clockwise up to the solid line position shown in FIG. 3. Lever 110 can now be pivoted counter-clockwise about pivotal axis 112 toward handle 20, i.e., by squeezing it toward the handle with the fingers of the hand holding the handle, to actuate the fastener driving mechanism.

When lever 110 is pivoted counter-clockwise as just described, the end of lever 110 inside the proximal end of connecting structure 30 contacts the proximal end 78 of driver 76 and drives driver 76 in the distal direction. The distal end of driver 76 contacts the proximal surface of knife-fastener pusher member 63, thereby driving member 63 in the distal direction and causing it to drive fasteners 120 out of fastener holder 52, through tissue 12, and into retainers 130 held in anvil assembly 54. Located slightly proximally of the distal end of fasteners 120 is knife surface 61 of knife-fastener pusher member 63 (see FIG. 9). After fasteners 120 have begun to pierce tissue 12, knife surface 61 begins to cut the tissue (see FIG. 10). As lever 110 is squeezed fully in the counter-clockwise direction, fasteners 120 lock into retainers 130 and knife surface 61 completely severs tissue 12 (see FIG. 11).

A strip 150 of somewhat flexible, resilient material, such as nylon, is positioned in the anvil assembly surface 53 parallel to knife surface 61 to provide a surface against which knife surface 61 can act to ensure cutting entirely through tissue 12. Strip 150 is fitted into indent 154 in anvil assembly surface 53.

The joining of the tissue is now complete and all that remains to be done is to remove the fastened tissue from the instrument. This is accomplished by releasing lever 110 which, because leaf springs 69 bias knife-fastener pusher member 63 in the proximal direction, causes knife-fastener pusher member 63 to retract into fastener holder 52. Actuator 70 is rotated in the counter-clockwise direction and fastener holder 52 pivots clockwise away from anvil assembly 54, in response to the pressure of leaf spring 51. Also, spring 81 biases alignment pin 80 away from anvil assembly 54 and thus retracts pin 80 into fastener holder 52. Tissue 12 can now be readily withdrawn from the instrument. Cartridge 50 is now removed from the instrument by pulling anvil assembly 54 out of distal leg 44. The expended cartridge is discarded and another cartridge is loaded in the instrument if additional tissue fastening is required during the surgical procedure. When the surgical procedure is complete, instrument 10 is cleaned and sterilized to prepare it for use in another surgical procedure.

It will be understood that the embodiment shown and described herein is only illustrative of the principles of the invention, and that various modifications can be made by those skilled in the art without departing from the scope and spirit of the invention. In particular, the invention has been described in conjunction with a disposable cartridge and a permanent, reusable instrument. The invention could also have been described in conjunction with a totally disposable instrument. When the entire instrument is disposable, as much of the instrument as possible is preferably made of relatively inexpensive materials such as plastic or the like. Preferably only those parts of the instrument which are subject to high stresses are made of metal.

Also, a cartridge of the type shown here can be used in instruments having many designs other than the particular instrument design herein described. Instruments having screw operated actuators (see, for example, FIGS. 18-21 of U.S. Pat. No. 4,354,628) or combinations of screw and lever actuators are also known in the art and are adaptable for use with the cartridge of this invention.

Finally, the preferred instrument of the invention has utilized fasteners and retainers as the means to seal the tissue. As described earlier, the invention equally is applicable to a cartridge designed to discharge metal surgical staples against an anvil as the means of sealing the tissue.

I claim:

1. A surgical fastener cartridge for use with an actuator assembly including a rigid frame having a U-shaped portion for simultaneously forming a plurality of surgical fasteners in body tissue comprising an anvil assembly;

a fastener holder pivotally connected to the anvil assembly adjacent one end of the anvil assembly, the fastener holder containing a plurality of surgical fasteners and including fastener driving means for substantially simultaneously driving all of the fasteners from the fastener holder;

means associated with the anvil assembly for allowing the cartridge to be removably mounted on the actuator frame so that the anvil assembly is adjacent a first leg of the U-shaped portion, so that the pivotal connection between the anvil assembly and the fastener holder is adjacent the base of the U-shaped portion, and so that the fastener holder is adjacent a second leg of the U-shaped portion, the fastener holder being movable relative to the frame when the cartridge is thus mounted on the frame so that when the fastener holder is pivoted away from the anvil assembly, the tissue to be fastened can be positioned between the anvil assembly and the fastener holder via the open side of the U-shaped portion;

spacer means located adjacent the side of the cartridge opposite the pivotal connection between the anvil assembly and the fastener holder for maintaining a predetermined minimum spacing between the anvil assembly and the fastener holder when the fastener holder is pivoted toward the anvil assembly;

the improvement comprising means associated with the spacer means for displacing tissue which extends beyond the ends of the fastener holder and anvil assembly to ensure that the fastener holder and anvil assembly are positioned correctly relative to each other after the fastener holder is pivoted toward the anvil assembly, said tissue displacing means comprising two surfaces sloping toward each other to form a knife-like edge to displace the tissue.

2. The cartridge defined in claim 1 in which the tissue displacing means further comprises two U-shaped surfaces extending from the surface of the fastener holder.

3. The cartridge defined in claim 1 further comprising alignment means located adjacent the side of the cartridge opposite the pivotal connection between the anvil assembly and the fastener holder fo aligning the anvil assembly and fastener holder in a direction parallel to the pivotal axis when the fastener holder is pivoted toward the anvil assembly to clamp the tissue to be fastened between the fastener holder and the anvil assembly, the alignment means comprising surface portions associated with each of the fastener holder and the anvil assembly, the surface portions being substantially perpendicular to the pivotal axis and being substantially rigid in a direction parallel to the pivotal axis, the surface portions associated with the fastener holder contacting the surface portions associated with the anvil assembly when the fastener holder is pivoted toward the anvil assembly to clamp the tissue.

4. The cartridge defined in claim 3 wherein the alignment means comprises a pin substantially perpendicular to the pivotal axis which extends into both the fastener holder and the anvil assembly when the fastener holder and anvil assembly are pivoted toward one another to clamp the tissue.

5. The cartridge defined in claim 4 wherein the tip of the pin is conically-shaped to enable it to penetrate tissue obstructing the aperture into which the pin is to be inserted when the fastener holder and anvil assembly are pivoted toward one another to clamp the tissue.

6. A surgical actuator assembly utilizing the surgical fastener cartridge of claim 1 or claim 3 comprising:

a rigid frame having a normally open peripheral portion for admitting body tissue to be fastened into an interior region of the frame; and clamp actuator means for pivoting the fastener holder toward the anvil assembly to clamp the tissue.

7. The cartridge defined in claim 1 or claim 3 further comprising knife means for cutting the tissue clamped between the fastener holder and the anvil assembly.

8. The cartridge defined in claim 7 wherein the distal end of the knife means is positioned proximally of the distal end of the fasteners held in the fastener holder and further comprising knife driving means associated with the fastener driving means for simultaneously driving the fasteners and the knife means from the fastener holder.

9. A surgical stapler for simultaneously forming a plurality of surgical fasteners in body tissue comprising a rigid frame having a U-shaped portion;

an anvil assembly mounted on a first leg of the U-shaped portion so that the anvil assembly is stationary relative to the frame;

a fastener holder disposed adjacent the second leg of the U-shaped portion and being pivotally mounted adjacent one end of the anvil assembly, the pivotal mounting being adjacent the base of the U-shaped portion, the fastener holder containing a plurality of surgical fasteners and including means for simultaneously driving the fasteners from the fastener holder;

actuator means mounted on the frame for pivoting the fastener holder toward the anvil assembly and actuating the means for driving the fasteners from the fastener holder;

an alignment pin mounted on said holder and having an end for piercing tissue disposed between said anvil assembly and said holder; and a spacer member at a location remote from the pivotal mounting of the fastener holder for contacting a portion of the anvil assembly opposite the fastener holder when the fastener holder is pivoted to span the normally open peripheral portion and for maintaining a gap between the remainder of the fastener holder and the anvil assembly;

wherein the spacer member is shaped so that, when tissue extends past the open peripheral portion of the retainer holder and fastener holder, the tissue pierced by said pin is displaced as the fastener holder closes against the anvil assembly to ensure that the proper minimum distance is achieved between the fastener holder and the anvil assembly.

10. A surgical fastener cartridge comprising an anvil assembly having an aperture therein;

a fastener holder pivotally connected at one end to said anvil assembly;

an alignment pin mounted on said fastener holder at an opposite end thereof for reception in said aperture of said anvil assembly, said pin having a shaped end for piercing tissue disposed between said anvil assembly and said holder and over said opening of said anvil assembly; and a spacer member mounted on said opposite end of said fastener for abutting said anvil assembly about said opening therein, said spacer member having surfaces shaped to displace the tissue pierced by said pin during pivoting of said holder towards said anvil assembly.

11. A surgical fastener cartridge as set forth in claim 10 wherein said pin end is conically-shaped.

12. A surgical fastener cartridge as set forth in claim 10 wherein said surfaces of said spacer member form a knife-like edge to displace tissue.

13. In combination, an anvil assembly having an aperture therein;

a fastener holder movably mounted relative to said anvil assembly;

an alignment pin mounted on said fastener holder at an opposite end thereof for reception in said aperture of said anvil assembly, said pin having a shaped end for piercing tissue disposed between said anvil assembly and said holder and over said opening of said anvil assembly; and a spacer member mounted on said opposite end of said fastener for abutting said anvil assembly about said opening therein, said spacer member having surfaces shaped to displace the tissue pierced by said pin during movement of said holder and anvil assembly towards each other.

14. The combination as set forth in claim 13 which further comprises means for moving said pin end from said holder into said aperture of said anvil assembly.

15. The combination as set forth in claim 14 wherein said pin end is conically-shaped.

16. The combination as set forth in claim 14 wherein said surfaces of said spacer member form a knife-like edge to displace tissue.

* * * * *

UNITED STATES PATENT AND TRADEMARK OFFICE
CERTIFICATE OF CORRECTION

PATENT NO. : 4,665,916

DATED : May 19, 1987

INVENTOR(S) : DAVID T. Green

It is certified that error appears in the above—identified patent and that said Letters Patent is hereby corrected as shown below:

Column 2, line 27 "alignment" should be -An alignment-
Column 5, line 44 "surface- 57c" should be -surface 57c-
Column 7, line 65 "fo" should be -for-.

Signed and Sealed this

Third Day of November, 1987

Attest:

Attesting Officer

DONALD J. QUIGG

Commissioner of Patents and Trademarks